US010646356B2

(12) United States Patent
Deshpande et al.

(10) Patent No.: US 10,646,356 B2
(45) Date of Patent: May 12, 2020

(54) ROBOTIC FINGER EXOSKELETON

(71) Applicant: Board of Regents, The University of Texas System, Austin, TX (US)

(72) Inventors: Ashish Deshpande, Austin, TX (US); Priyanshu Agarwal, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1001 days.

(21) Appl. No.: 15/184,547

(22) Filed: Jun. 16, 2016

(65) Prior Publication Data

US 2016/0296345 A1 Oct. 13, 2016

Related U.S. Application Data

(60) Provisional application No. 61/917,411, filed on Dec. 18, 2013.

(51) Int. Cl.
*A61H 1/00* (2006.01)
*A61F 2/58* (2006.01)
(Continued)

(52) U.S. Cl.
CPC .......... *A61F 2/586* (2013.01); *A61H 1/0288* (2013.01); *A63B 21/152* (2013.01);
(Continued)

(58) Field of Classification Search
CPC .......... A61H 1/0288; A61H 2201/0065; A61H 2201/0165; A61H 2201/1215; A61H 2201/149; A61H 2201/1635; A61H 2201/165; A61H 2201/1676; A61H 2201/501; A61H 2201/5038;
(Continued)

(56) References Cited

U.S. PATENT DOCUMENTS 8,951,303 B2 * 2/2015 Dehoff .................. A61F 2/583
623/26
2019/0015287 A1 * 1/2019 Witte ...................... A61H 1/00
2019/0151181 A1 * 5/2019 Lince .................. A61H 1/0288

FOREIGN PATENT DOCUMENTS

EP 2345951 A2 7/2011
WO 2009/016478 A2 2/2009

OTHER PUBLICATIONS

International Preliminary Report on Patentability for International Application No. PCT/US2014/071049, dated Jun. 21, 2016, 9 pages.
(Continued)

*Primary Examiner* — Steven O Douglas
(74) *Attorney, Agent, or Firm* — Baker Botts L.L.P.

(57) ABSTRACT

The present disclosure includes a finger exoskeleton including a plurality of joints and a plurality of sensors configured to measure rotation of at least some of the plurality of joints of the finger exoskeleton. The finger exoskeleton also includes a series elastic actuator comprising a spring element, the series elastic actuator configured to rotate at least one of the plurality of joints. The finger exoskeleton also includes a computing device configured to control operation of the series elastic actuator based on a torque of the at least one of the plurality of joints, the torque determined at least based on the spring element and rotation of the at least one of the plurality of joints. The present disclosure also includes associated methods and hand exoskeletons.

19 Claims, 10 Drawing Sheets

(51) Int. Cl.
  *A61H 1/02* (2006.01)
  *B25J 9/00* (2006.01)
  *A63B 21/00* (2006.01)
  *A61F 2/50* (2006.01)

(52) U.S. Cl.
  CPC ......... *A63B 21/4019* (2015.10); *B25J 9/0006* (2013.01); *A61F 2002/5007* (2013.01); *A61F 2002/5093* (2013.01); *A61H 2201/0165* (2013.01); *A61H 2201/1215* (2013.01); *A61H 2201/149* (2013.01); *A61H 2201/165* (2013.01); *A61H 2201/1635* (2013.01); *A61H 2201/1676* (2013.01); *A61H 2201/501* (2013.01); *A61H 2201/5038* (2013.01); *A61H 2201/5043* (2013.01); *A61H 2201/5046* (2013.01); *A61H 2201/5069* (2013.01); *A61H 2205/067* (2013.01)

(58) Field of Classification Search
  CPC .... A61H 2201/5043; A61H 2201/5046; A61H 2201/5069; A61H 2205/067; A61F 2/586; A63B 21/4019; A63B 21/152
  See application file for complete search history.

(56) References Cited

OTHER PUBLICATIONS

International Search Report and Written Opinion for International Application No. PCT/US2014/071049, dated May 6, 2015, 14 pages.
A. Chiri et al's "Handexos: Towards a Support Device for Hand Activities and Telpresence", 19 pages.

* cited by examiner

ROBOTIC FINGER EXOSKELETON

RELATED APPLICATIONS

This application is a continuation application of International Application No. PCT/US2014/071049 filed Dec. 18, 2014, which designates the United States, which claims priority to U.S. Provisional Application Ser. No. 61/917,411 filed Dec. 18, 2013, and which is incorporated herein by reference in its entirety.

STATEMENT OF GOVERNMENT INTEREST

This invention was made with government support under Grant no. CNS1135949 awarded by the National Science Foundation. The government has certain rights in the invention

TECHNICAL FIELD OF THE DISCLOSURE

This disclosure relates generally to biomechanics and robotics, and in particular, to a robotic finger exoskeleton.

BACKGROUND

Exoskeletons are mechatronic systems worn by a person in such a way that a direct transfer of mechanical power from the exoskeleton occurs. These robotic mechanisms have been applied in a variety of settings, for example, telemanipulation, man-amplification, rehabilitation, and to assist impaired human motor control. However, many of these applications of exoskeleton devices have yet to find widespread use, acceptance, or practicality.

One example area in which these devices have been proposed is the treatment of stroke. Stroke affects thousands of Americans every year and the recovery process is long, difficult, and costly. The use of a finger robotic exoskeleton may potentially reduce the length, difficulty, and cost of this recovery process.

A human index finger has three joints. The joint closest to the palm of the hand (the metcarpophalangeal (MCP) joint), the next joint (the proximal interphalangeal (PIP) joint), and the last joint (the distal interphanalgeal (DIP) joint). A human thumb also has three joints. The joint closest to the palm of the hand is the carpometacarpal (CMC) joint, the next joint is the MCP joint, and the joint furthest from the palm of the hand is the interphalangeal (IP) joint.

Various efforts have been proposed to provide a robotic exoskeleton for fingers. However, there still exists a need in the art for improvements in this field.

SUMMARY

In one example embodiment, the present disclosure may include a finger exoskeleton comprising a plurality of joints and a plurality of sensors configured to measure rotation of at least some of the plurality of joints of the exoskeleton finger. The finger exoskeleton may also include a series elastic actuator comprising a spring element, the series elastic actuator configured to rotate at least one of the plurality of joints. The finger exoskeleton may also include a computing device configured to control operation of the series elastic actuator based on a torque of the at least one of the plurality of joints, the torque determined at least based on the spring element and rotation of the at least one of the plurality of joints.

In another example embodiment, the present disclosure may include a method comprising measuring a first rotation of a joint of a robotic finger exoskeleton and detecting a second rotation of a motor coupled to a series elastic actuator. The method may also include determining a torque of the joint of the robotic finger exoskeleton based at least on the first rotation and a spring element of the series elastic actuator and modifying operation of the series elastic actuator based on the torque.

In an additional example embodiment, the present disclosure may include a hand exoskeleton comprising a plurality of finger exoskeletons, each finger exoskeleton comprising a plurality of joints and a plurality of sensors configured to measure rotation of at least some of the plurality of joints of the finger exoskeleton. Each finger exoskeleton may also include a series elastic actuator comprising a spring element, the series elastic actuator configured to rotate at least one of the plurality of joints. The hand exoskeleton may also include a computing device configured to control operation of the series elastic actuator based on a torque of the at least one of the plurality of joints, the torque determined at least based on the spring element and rotation of the at least one of the plurality of joints.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

The present disclosure relates to a robotic finger exoskeleton. The robotic finger exoskeleton may include a plurality of joints and a plurality of sensors to measure rotational position of the joints. The robotic finger exoskeleton may also include a series elastic actuator (SEA) with a spring element so that when a motor is actuated to rotate one of the joints, the torque on the joint may also be calculated. This may allow the robotic finger exoskeleton to operate in a force control mode of operation rather than merely a position control mode. The robotic finger exoskeleton may also include sliding joints or linear bearings to reduce force on the joints of the finger of the user of the robotic exoskeleton finger.

Figure 1:
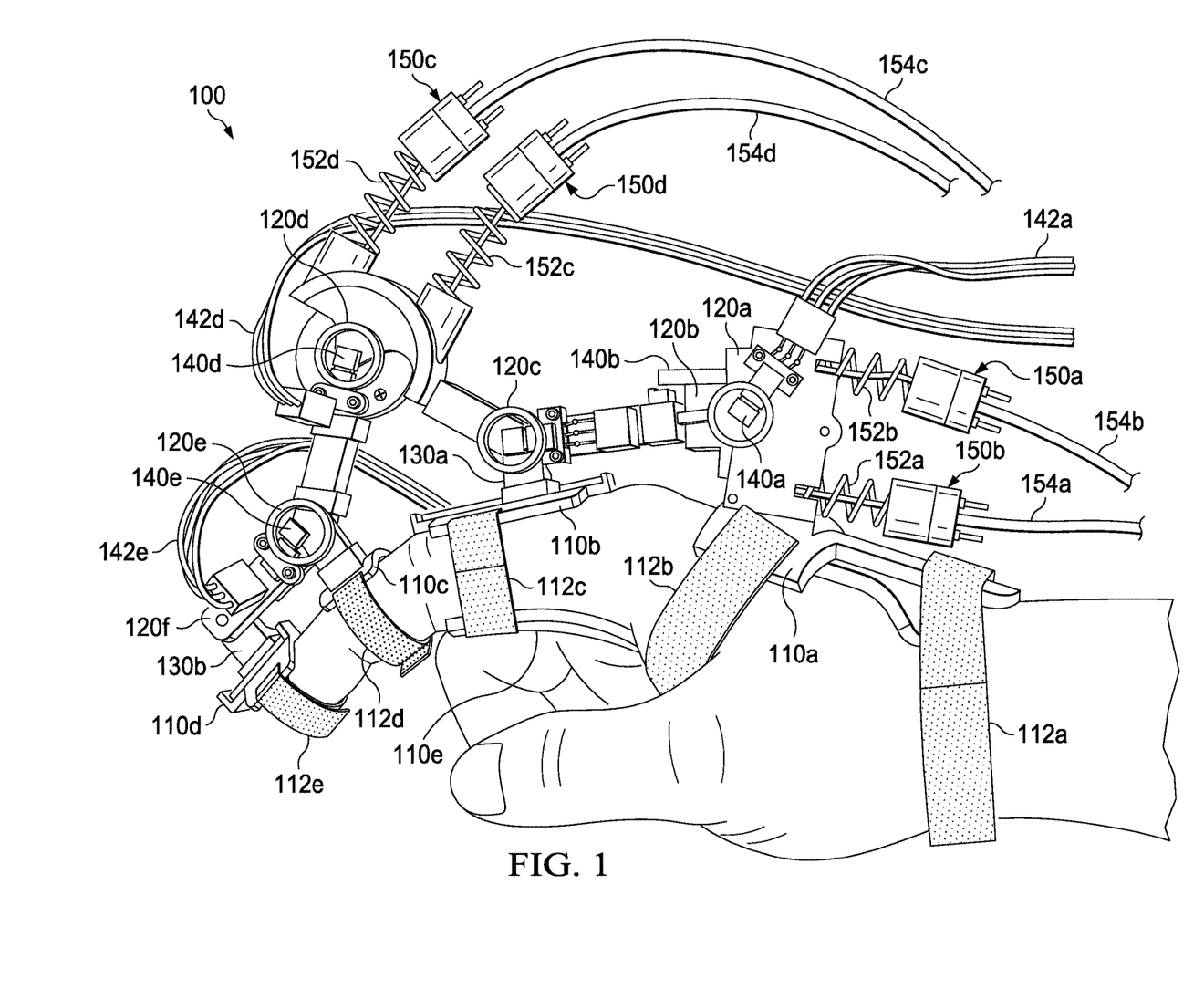
FIG. 1 illustrates an example of a robotic finger exoskeleton, in accordance with at least some embodiments of the present disclosure.

FIG. 1 illustrates an example embodiment of a robotic finger exoskeleton. A robotic finger exoskeleton 100 may include a plurality of mounting components 110a, 110b, 110c, 110d, and 110e. These may be coupled with attachment straps 112a, 112b, 112c, 112d, and 112e. Finger exoskeleton 100 may also include a plurality of joints, 120a, 120b, 120c, 120d, 120e, and 120f. Finger exoskeleton 100 may additionally include sliding joints 130a and 130b. Finger exoskeleton 100 may also include sensors 140a, 140b, 140c, 140d, and 140e, which may be coupled to data cables 142 (e.g. data cables 142a, 142d, and 142e). Finger exoskeleton 100 may further include series elastic actuators (SEAs) 150a, 150b, 150c, and 150d. These may include spring elements 152a, 152b, 152c, and 152d.

Mounting components 110 may be any component or device used to wrap finger exoskeleton 100 about a finger of a user of finger exoskeleton 100. For example, mounting components 110 may be shaped to provide an anatomically shaped component providing a comfortable and ergonomic attachment of finger exoskeleton 100 to the user. Mounting components 110 may be padded or may merely serve a padding function (for example, mounting component 110e may be a high-density rubber foam pad). Mounting components 110 may have various other components of finger exoskeleton 100 attached thereto. For example, as shown in FIG. 1, mounting component 110a may have framework supporting joints 120a, 120b, and sensors 140a and 140b attached thereto; mounting component 110b may have sliding joint 130a attached thereto; mounting component 110c may have framework supporting joint 120e and sensor 140e attached thereto; and mounting component 110d may have sliding joint 130b attached thereto. Mounting components 110 may be created using three-dimensional printing, or in other words, additive manufacturing. For example, mounting components 110 may be manufactured using selective laser sintering (SLS). In some embodiments, mounting components 110 may be configured to support more than one finger exoskeleton 100. For example, mounting component 110a may support up to five distinct finger exoskeletons.

Mounting components 110 may be attached to a user of finger exoskeleton 100 using attachment straps 112. Attachment straps 112 may be any device or component used to fix mounting components 110 to a user of finger exoskeleton 100. For example, attachment straps 112 may include velcro straps, buckles, snaps, or other attachment methods. Attachment straps 112 may be readily and rapidly adjustable to allow ease in attaching or removing finger exoskeleton 100. The material and attachment method of attachment straps 112 may be selected to provide a comfortable fit for the user of finger exoskeleton 100, while allowing for a secure attachment of finger exoskeleton 100. More than one attachment strap 112 may attach a single mounting component to a user. For example, mounting component 110a may be attached to a user using attachment straps 112a and 112b. In some embodiments, more than one mounting component 110 may be attached using a single attachment strap 112. For example, mounting components 110b and 110e may be attached to a user using attachment strap 112c. While attachment straps 112a through 112e are illustrated in FIG. 1, it will be appreciated that any number of attachment straps 112 may be used to securely and comfortably attach finger exoskeleton 100 to a user.

Joints 120 may be any juncture of finger exoskeleton at which movement may occur. The movement may be rotation, lateral motion, or any other motion. Joints 120 may be hinge joints configured to provide rotation about a pivot point. In some embodiments, joints 120 may use ultra-miniature rotary ball bearings. In some embodiments, some of joints 120 may be coupled to a motive force while others may only provide for passive motion. For example, joints 120 may be coupled to series elastic actuators (SEAs) 150 to provide motive force. Joints 120 may be manufactured using any suitably rigid and durable material to allow repeated movement of the joint. For example, joints 120 may be manufactured using three-dimensional printing like SLS. Joints 120 may also be manufactured using stainless steel, aluminum, hard plastic, or other suitable material. The number and amount of movement of joints 120 may be selected such that finger exoskeleton 100 provides comfortable and kinematically accurate movement. For example, finger exoskeleton 100 may include a first joint 120a which is coupled to SEAs 150a and 150b. SEAs 150 and associated spring elements 152 may be described in more detail with respect to FIGS. 4 through 6.

Joint 120a may replicate and provide motive force for part of the motion of the MCP joint. For example, joint 120a may support flexion and extension of the MCP joint. Joint 120a may be coupled to mounting component 110a via framework of finger exoskeleton 100. Joint 120a may also be connected to joint 120b via framework. Joint 120b may provide passive motion to the MCP joint, for example, allowing lateral motion of a user's finger about the MCP joint. Joint 120b may be connected to joint 120c via framework. Joint 120c may be a hinge joint allowing passive rotation about joint 120c. Joint 120c may be connected to joint 120d through framework. Joints 120c and 120d may cooperatively replicate the motion of the PIP joint. For example, the rotation about joints 120c and 120d may allow movement in the same plane passing approximately through the center of the user's finger, or in other words, a sagittal plane of the finger. Joint 120d may be coupled to SEAs 150c and 150d which may provide motive force to joint 120d. This may provide motive force to finger exoskeleton 100 when replicating the movement of the PIP joint. Joint 120d may be connected to joint 120e via framework. Joint 120e may provide passive motion to assist in the replication of the motion of the DIP joint. In some embodiments, the motive force generated at joint 120d may also be coupled to joints 120e and 120f. In this way, when a user flexes or extends their finger about the PIP joint, the DIP joint is also flexed or extended to a certain extent. This may not be a one to one linkage when connecting the motive force of joint 120d to joint 120e, and the amount of motive force transferred may be selected to match the typical relationship among contraction of the two human joints. Joint 120f may provide passive rotation motion to facilitate replication of the motion about the DIP joint.

In addition to joints 120, finger exoskeleton 100 may also include sliding joints 130. Sliding joint 130 may include a slider and a track that are coupled such that the slider may slide along the track. This may provide a motion at the joint defined by the track. For example, this may be a linear motion if the track follows a linear path. In some embodiments, sliding joint 130 may use ultra-miniature linear ball bearings. Sliding joints 130 may translate any force generated by the exoskeleton, which is not normal to the joint, into a sliding motion. This may prevent forces being generated against the joints themselves. For example, a force generated at joint 120a may not be directly normal to the finger phalange. Thus, whatever portion of the force was not normal may be exerted against the MCP joint. By using sliding joint 130a, rather than exerting the non-normal force against the MCP joint, the force instead causes sliding joint 130a to slide. In other words, employing sliding joints 130 as the interface between the finger phalange and finger exoskeleton 100 may ensure that only normal reaction forces are applied on the finger phalanges in all configurations. Any lateral force may result in the translation of the slider until only the normal reaction force exists between the two. If a sliding joint 130 is not used, the normal reaction force component may contribute to generating a moment at the joint while the lateral component may simply load the joint without resulting in any joint moment.

In some embodiments, only some of the joints may utilize sliding joints 130. For example, as shown in FIG. 1, while the MCP and DIP joints may utilize sliding joints 130 to protect against non-normal forces, the PIP joint may not utilize a sliding joint. This may allow for greater range of motion without requiring an additional motor. For example, by using joints 120c and 120d to replicate the motion of the PIP joint, the PIP joint has much greater range of motion without interference from the exoskeleton. However, if sliding joint 130 were used at mounting component 110c rather than a fixed point connection, an additional motor may be introduced to cover the additional degree of freedom. In some embodiments, each finger joint may be protected by sliding joints 130. This may lead to the coupling of additional motors to some of joints 120 of finger exoskeleton 100.

In some embodiments, the finger phalanges are used as part of the linkage with finger exoskeleton 100, including joints 120, sliding joints 130, and framework, to avoid any misalignment problems. For example, there may be three phalange-exoskeleton closed-loop kinematic chains to avoid joint axes misalignment problem. The MCP chain may consist of four links with three rotational joints (i.e., joints 120a, 120c and the MCP joint) and one translational joint (i.e., sliding joint 130a) resulting in one degree of freedom. In other words, as a four-bar linkage may be created there may be only a single degree of freedom and only a single motive source may be used to replicate the motion of the joint. The PIP chain may consist of four links with four rotational joints (assuming the first chain is fixed) (i.e., joint 120c, joint 120d, joint 120e and DIP joint), resulting in one degree of freedom. Similarly, the four-bar linkage may use a single motive force to replicate the motion of the joint. The DIP chain may consist of four links with three rotational joints (i.e., joint 120e, 120f and the DIP joint) and one translational joint (sliding joint 130b) leading to one degree of freedom. In the embodiment shown in FIG. 1, the motion of the DIP joint is not powered by motive force. However, in some embodiments, it may be by attaching a motor to joint 120f.

Finger exoskeleton 100 may also include sensors 140. Sensors 140 may be any device or component used to measure positional information of finger exoskeleton 100. For example, sensors 140 may be coupled to and measure the amount of rotation about joints 120. Various features and embodiments of sensors 140 may be discussed in more detail below with reference to FIG. 3. Information and/or data sensed by sensors 140 may be passed along data cables 142 to a computing device. In some embodiments, sensors 140 may wirelessly transmit sensed information and/or data, rather than transmitting the data along data cables 142. In some embodiments, information and/or data from sensors 140 may be collected at one or more points on finger exoskeleton 100 and then passed from the one or more collection points to a computing device.

Figure 2:
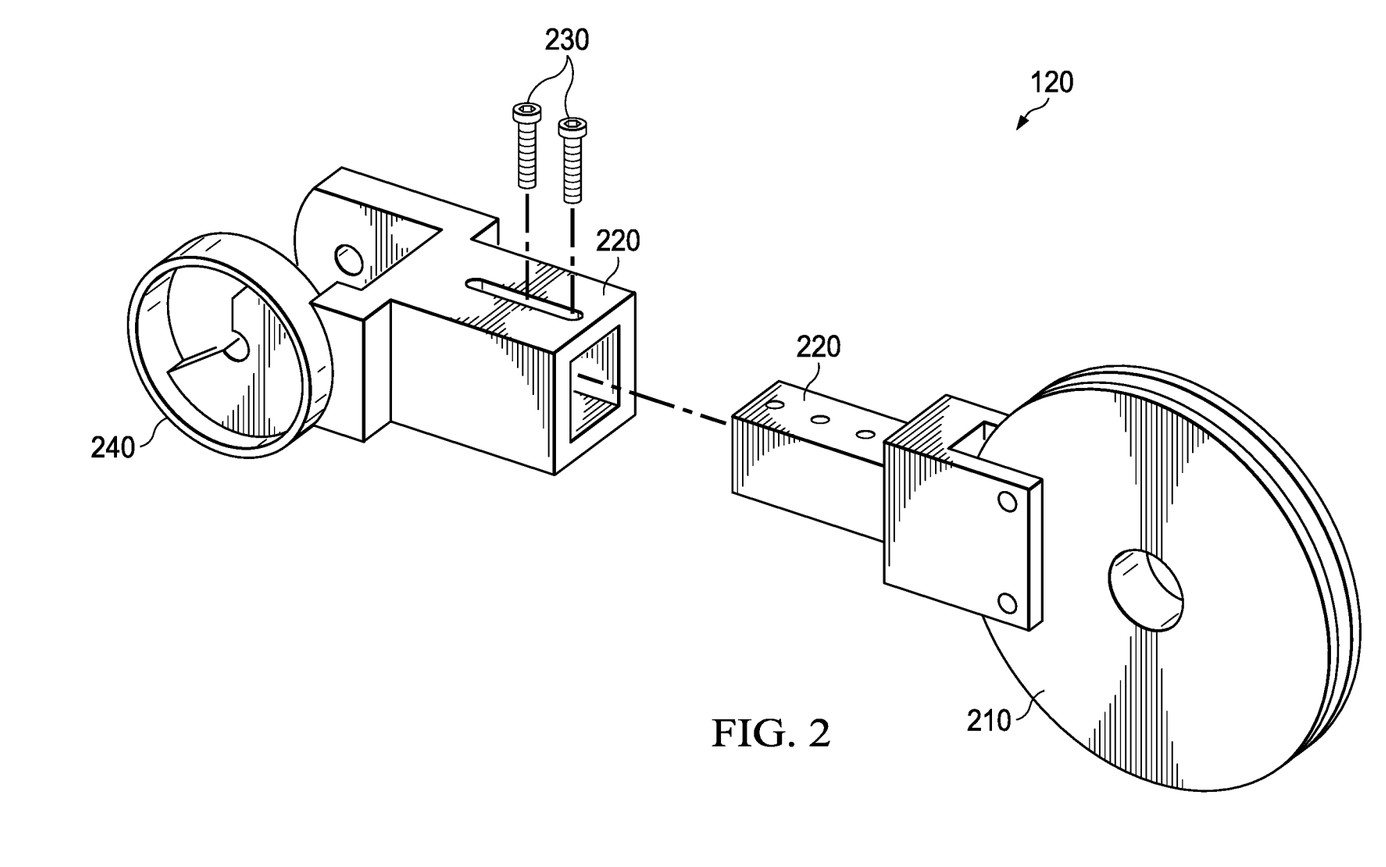
FIG. 2 illustrates an example of portions of a joint of a robotic finger exoskeleton, in accordance with at least some embodiments of the present disclosure.

FIG. 2 illustrates an example of portions of joint 120 of robotic finger exoskeleton 100. For example, joint 120 may include a pulley 210, framework 220, connecting members 230, and sensor housing 240. As shown in FIG. 2, various portions of the framework of finger exoskeleton 100 may be adjustably sized such that portions of the framework may be shortened or lengthened depending on the size and physiology of the user of finger exoskeleton 100 and/or the desired range of motion. For example, various slots in members of framework 220 of finger exoskeleton 100 may be used with connecting members 230 (e.g., screws, nuts, bolts, tabs, etc.) within the slots to connect two slidably engaged members of framework 220 of finger exoskeleton 100. If a different size is desired, connecting members 230 may be loosened and the two slidably engaged members of framework 220 may be slid past each other. Once a desired size is reached, connecting member 230 within the slot may be retightened. This may allow for a customizable framework for finger exoskeleton 100 which may be easily and rapidly re-sized or re-oriented based on the user of finger exoskeleton 100. Any number of connecting members 230 and/or slots may be used to provide one or more directions of adjustability. Additionally, connections between framework and mounting components 110 may be adjustable. For example, the orientation and location of the framework coupled to mounting component 110a may be adjusted based on the user of finger exoskeleton 100. As used herein, the term "framework" may refer to structural members of finger exoskeleton 100, including mechanical linkages. It will be appreciated that other adjustable systems may be used to change the sizes of various portions of the framework of finger exoskeleton 100, and that the use of slots is merely an illustrative example.

Figure 3:
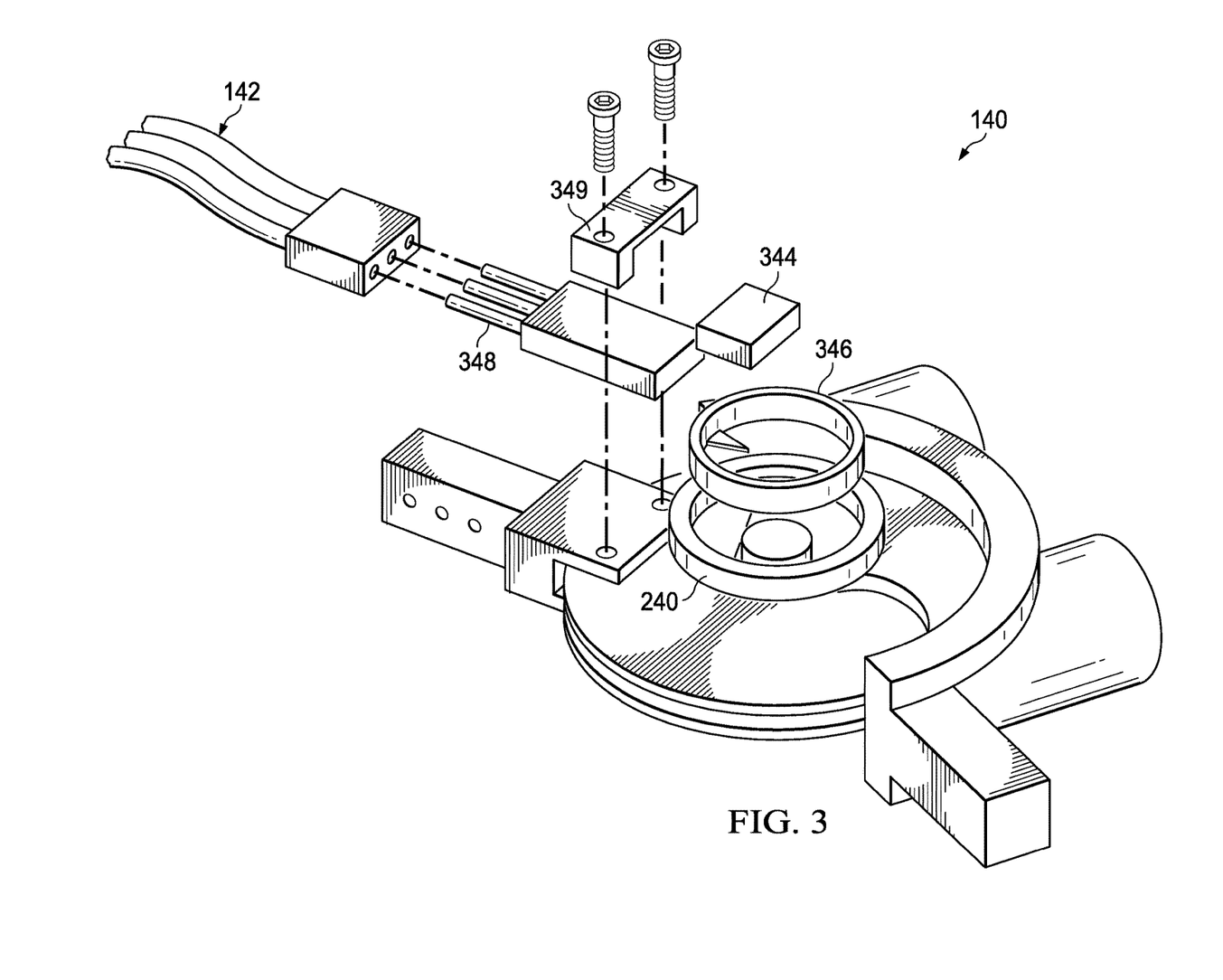
FIG. 3 illustrates an example of portions of a sensor of a robotic finger exoskeleton, in accordance with at least some embodiments of the present disclosure.

FIG. 3 illustrates an example of portions of a sensor of a robotic finger exoskeleton. For example, sensor 140 may be a magnetic angle sensor module. In such an embodiment, sensor 140 may include a sensor housing 240 containing or holding a measuring band 346. Measuring band 346 may be a diametrically magnetized ring magnet. Sensor housing 240 may be attached to or unitarily formed with one side of joint 120. A sensing chip 344 may be attached to the other side of joint 120 that is rotating relative to the side with sensor housing 240 using connecting members 349. Sensing chip 344 may also be disposed in proximity to or, in some embodiments, within measuring band 346. As rotation occurs at joint 120, sensing chip 344 may rotate relative to measuring band 346. As sensing chip 344 rotates relative to measuring band 346, sensing chip 344 may generate electrical signals, data, and/or information indicative of the amount of rotation occurring at joint 120. This information may be output to pins 348. Pins 348 may be configured to couple with data cable 142 to convey the information to a computing device.

Figure 4:
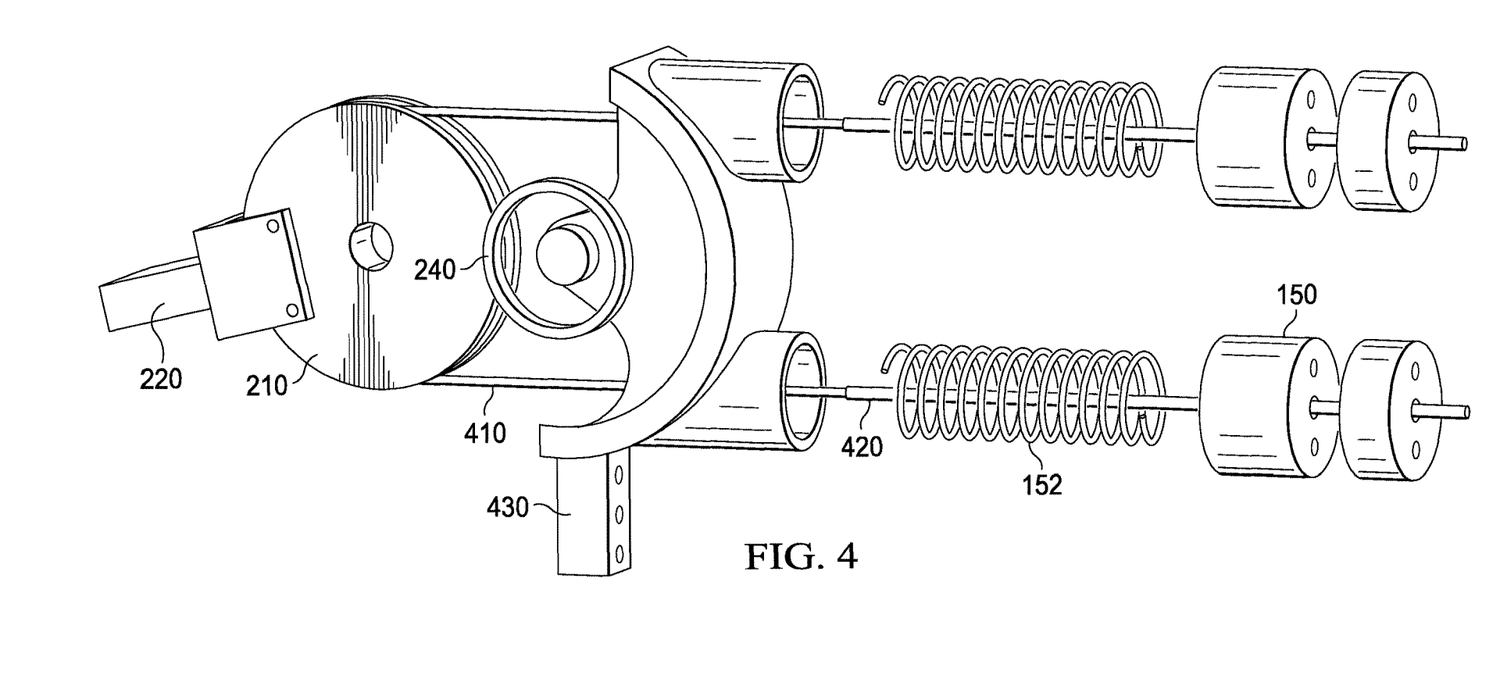
FIG. 4 illustrates an example of portions of a series elastic actuator, in accordance with at least some embodiments of the present disclosure.

FIG. 4 illustrates an example of portions of a series elastic actuator. In some embodiments, series elastic actuator 150 may include Bowden cables. As shown in FIG. 4, pulley 210 of joint 120 may have a cable 410 going around the circumference of pulley 210. Pulley 210 may be caused to rotate as cable 410 is moved. Framework 220 may be attached to pulley 210 such that as pulley 210 moves, framework 220 and the entire kinematic chain may also move. On the other side of joint 120, framework 430 may be unitarily formed with sensor housing 240 and remain stationary relative to the rotation of pulley 210 as it rotates due to the motion of cable 410. Cable 410 may be partially contained within a sheath 420. Cable 410 may be made of any suitable material, such as an FEP (fluorinated ethylene propylene) coated stainless steel 0.026 inch diameter wire rope to reduce friction between cable 410 and sheath 420. Sheath 420 may be made of nylon. For each end of cable 410 connected to pulley 210, there may be a spring element 152 attached to sheath 420. When a motor actuates pulley 210, it may first compress spring element 152. The entire kinematic chain may be actuated in the center plane of the mechanism using SEA 150 so that little or no sideways forces may be applied on the finger while finger exoskeleton 100 is actuated.

The use of a passive series elastic element in the transmission mechanism may provide a means for accurately estimating tension in cable 410. For example, the tension may be estimated using the displacement measurements obtained using sensor 140 mounted at joint 120 as well as measuring displacement at a motor coupled to the other end of cable 410.

In some embodiments, this estimation may be governed by the equations:

$$\tau_{joint} = K_{spring}(\theta_{joint} - \theta_{actuator})$$
$$F_{tension} = \frac{\tau_{joint}}{r_{joint}}$$

Figure 5:
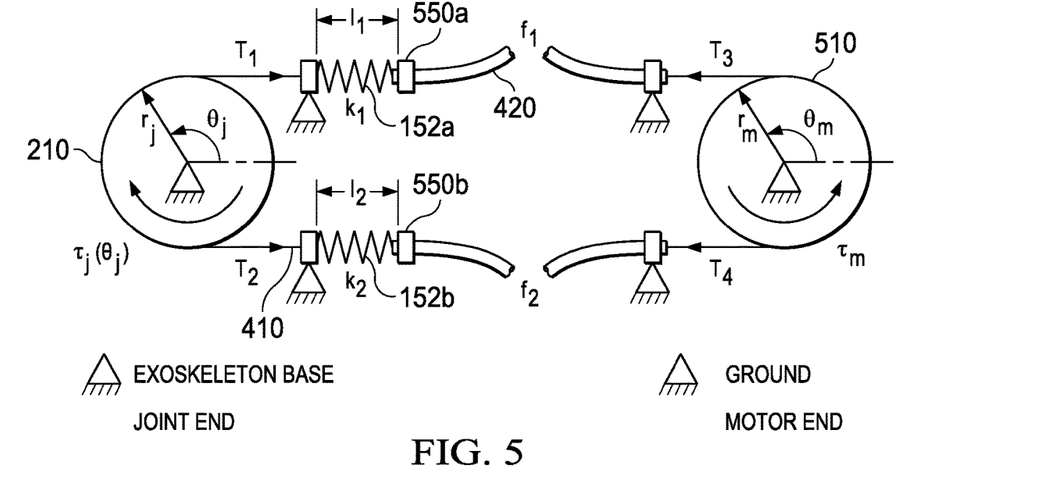
FIGS. 5 and 6 illustrate alternative examples of portions of a series elastic actuator, in accordance with at least some embodiments of the present disclosure.
Figure 6:
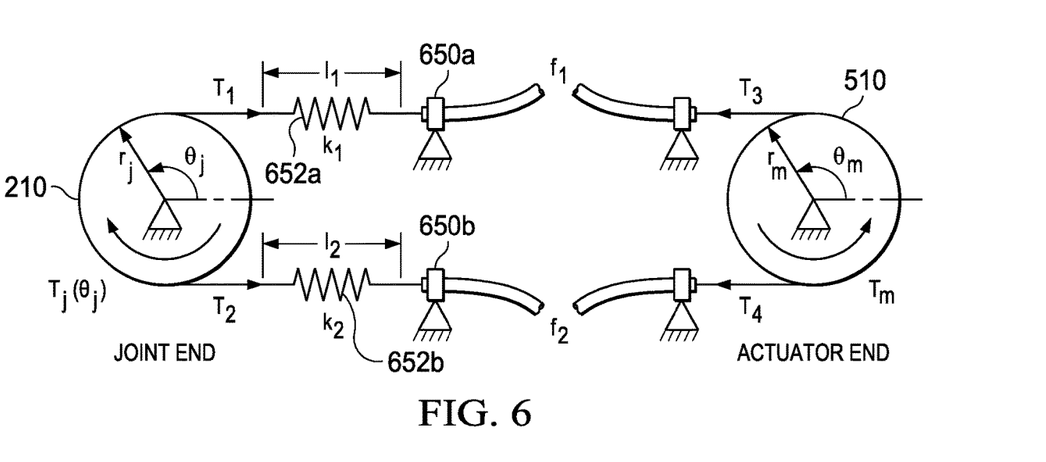

FIGS. 5 and 6 illustrate alternative examples of portions of a series elastic actuator. As shown in FIG. 5, cable 410 may extend about the circumference of pulley 210. Spring element 152a may be attached to sheath 420 via fixing member 550a. Spring element 152a may also be fixed to the base or framework of finger exoskeleton 100. Fixing member 550a and/or 550b may be any device or component to clamp or fix spring element 152a and/or 152b to a component (e.g. sheath 420 or framework). Motor 510 may also be coupled to cable 410. Sheath 420 may be fixed proximate motor 510. In some embodiments, as motor 510 is actuated, it may cause the rotation of pulley 210. If movement at pulley 210 is resisted, tension in cable 410 may be increased and spring elements 152a and/or 152b may be compressed. As described previously, using the amount of rotation of motor 510, pulley 210, and compression of spring elements 152a and/or 152b, the tension in cable 410 may be estimated, which may be correlated with the torque experienced at the joint. The embodiment shown in FIG. 5 may reduce the space requirement on finger exoskeleton 100 as spring element 152a and/or 152b compresses in operation, rather than being stretched (for example, as shown in FIG. 6). In addition, because spring element 152a and/or 152b reduces in length as finger exoskeleton 100 operates, this may avoid interference with other components.

FIG. 6 operates in a similar manner to the embodiment shown in FIG. 5. However, rather than using compressive spring elements, extension spring elements 652a and/or 652b are directly coupled to cable 410. In this embodiment, as the tension in cable 410 increases, spring elements 652a and/or 652b may experience a tensile force as they are expanded, rather than being compressed. The same estimations described with reference to FIG. 5 with respect to tension in cable 410 and torque at the joint may be utilized; however, rather than a compression spring element, an extension spring element may be used.

Figure 7:
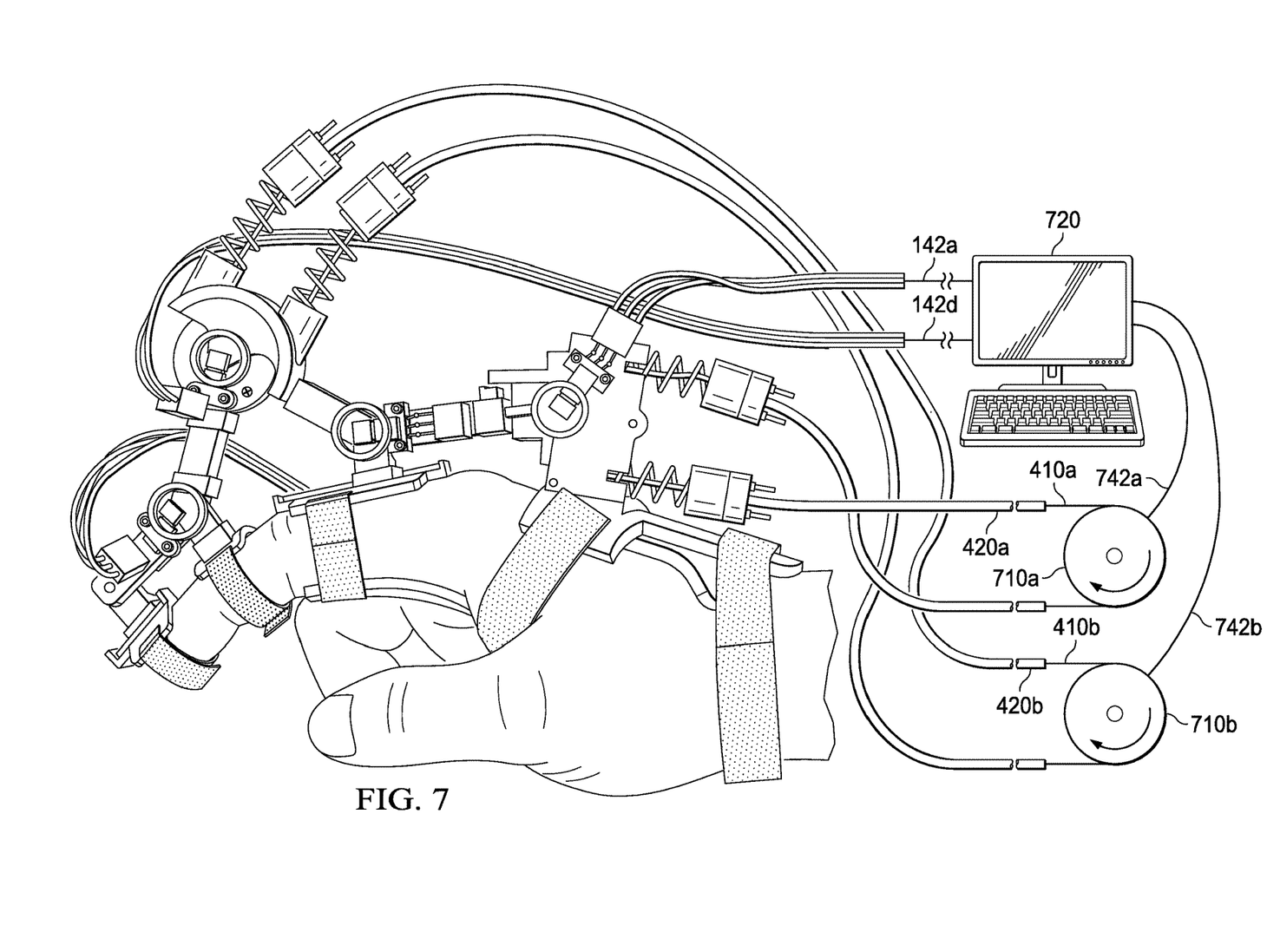
FIG. 7 illustrates an example of a robotic finger exoskeleton coupled with a computing device and motors, in accordance with at least some embodiments of the present disclosure.

FIG. 7 illustrates an example of a robotic finger exoskeleton coupled with a computing device and motors. As shown in FIG. 7, data cables 142a and 142d may be coupled with a computing device 720. Computing device 720 may be coupled to motors 710a and 710b via data cables 742a and 742b.

Computing device 720 may include any instrumentality or aggregate of instrumentalities operable to compute, calculate, determine, classify, process, transmit, receive, retrieve, originate, switch, store, display, communicate, manifest, detect, record, reproduce, handle, or utilize any form of information, intelligence, or data for business, scientific, control, or other purposes. For example, computing device 720 may be a personal computer (e.g., desktop or laptop), tablet computer, mobile device (e.g., personal digital assistant (PDA) or smart phone), server (e.g., blade server or rack server), a network storage device, or any other suitable device and may vary in size, shape, performance, functionality, and price. Computing device 720 may include random access memory (RAM), one or more processing resources such as a central processing unit (CPU) or hardware or software control logic, ROM, and/or other types of nonvolatile memory. Additional components of computing device 720 may include one or more disk drives, one or more network ports for communicating with external devices as well as various input and output (I/O) devices, such as a keyboard, a mouse, touchscreen, and/or a video display. Computing device 720 may also include one or more buses operable to transmit communication between the various hardware components.

For the purposes of this disclosure, computer-readable media may include any instrumentality or aggregation of instrumentalities that may retain data and/or instructions for a period of time. Computer-readable media may include, without limitation, storage media such as a direct access storage device (e.g., a hard disk drive or floppy disk), a sequential access storage device (e.g., a tape disk drive), compact disk, CD-ROM, DVD, random access memory (RAM), read-only memory (ROM), electrically erasable programmable read-only memory (EEPROM), and/or flash memory; as well as communications media such as wires, optical fibers, microwaves, radio waves, and other electromagnetic and/or optical carriers; and/or any combination of the foregoing.

A processor may include any system, device, or apparatus configured to interpret and/or execute program instructions and/or process data, and may include, without limitation a microprocessor, microcontroller, digital signal processor (DSP), application specific integrated circuit (ASIC), or any other digital or analog circuitry configured to interpret and/or execute program instructions and/or process data. In some embodiments, a processor may interpret and/or execute program instructions and/or process data stored in memory and/or another component of a computing device. Computing device 720 may include any suitable number of processors.

Memory may be communicatively coupled to a processor and may include any system, device, or apparatus configured to retain program instructions and/or data for a period of time (e.g., computer-readable media). Memory may include random access memory (RAM), electrically erasable programmable read-only memory (EEPROM), a PCMCIA card, flash memory, magnetic storage, opto-magnetic storage, or any suitable selection and/or array of volatile or non-volatile memory that retains data after power computing device 720 is turned off. Computing device 720 may include any suitable number and variety of memories.

Computing device 720 may be configured to receive position information from one or more sensors 140 of finger exoskeleton 100, for example, via data cables 142a and 142d. Computing device 720 may also receive position information regarding motors 710a and/or 710b. This information may be utilized to estimate the tension in cables 410a and/or 410b and may then be used to estimate the torque experienced at a given joint coupled to motor 710a and/or 710b. In some embodiments, data cables 742a and/or 742b may be bi-directional cables, such that computing device 720 may direct the actuation of motors 710 in addition to receiving data regarding position of motors 710. For example, computing device 720 may direct the speed, power, duration, etc. of motors 710. In some embodiments, computing device 720 may alter a planned motor actuation based on an estimated torque at a joint.

In some embodiments, finger exoskeleton 100 may operate in a force control mode rather than a position control mode. In a force control mode, finger exoskeleton 100 may account for forces experienced at a joint and actuate motors associated with finger exoskeleton 100 based on those forces. As described above, by using SEAs 150, forces experienced at various joints of finger exoskeleton 100 may be determined. In some embodiments, the various calculations and directions of finger exoskeleton 100 may be performed by computing device 720. In a position control mode, finger exoskeleton 100 may operate based on the position of various components of finger exoskeleton 100. For example, finger exoskeleton operating under position control may rotate a given joint a certain number of degrees, regardless of the force required to do so. This may cause pain or discomfort for a user of finger exoskeleton 100. For example, if finger exoskeleton 100 were used as a rehabilitation device and a patient were to have stiff fingers that were painful to move beyond a certain point, the torque experienced at the joint may increase as that point is reached. Computing device 720 may recognize the force generated and alter the planned amount of motor actuation based on the unexpected increase in torque at the joint if operating under a force control mode of operation. In contrast, when operating under a position control mode of operation, finger exoskeleton 100 may move the painful joint to the planned rotation, regardless of the force required to do so. This may result in the user experiencing pain in the stiff joint.

In some embodiments, motors 710 may be located remotely from finger exoskeleton 100. For example, motors 710 may be located further up the arm or on a backpack for the user of finger exoskeleton. Alternatively, motors 710 may be located on a table or other surface by the user. A limiting factor for the location of motors 710 may be the reach of cable 410. For example, motors 710 may be in a completely different room from finger exoskeleton 100 as long as cable 410 could reach far enough.

Figure 8:
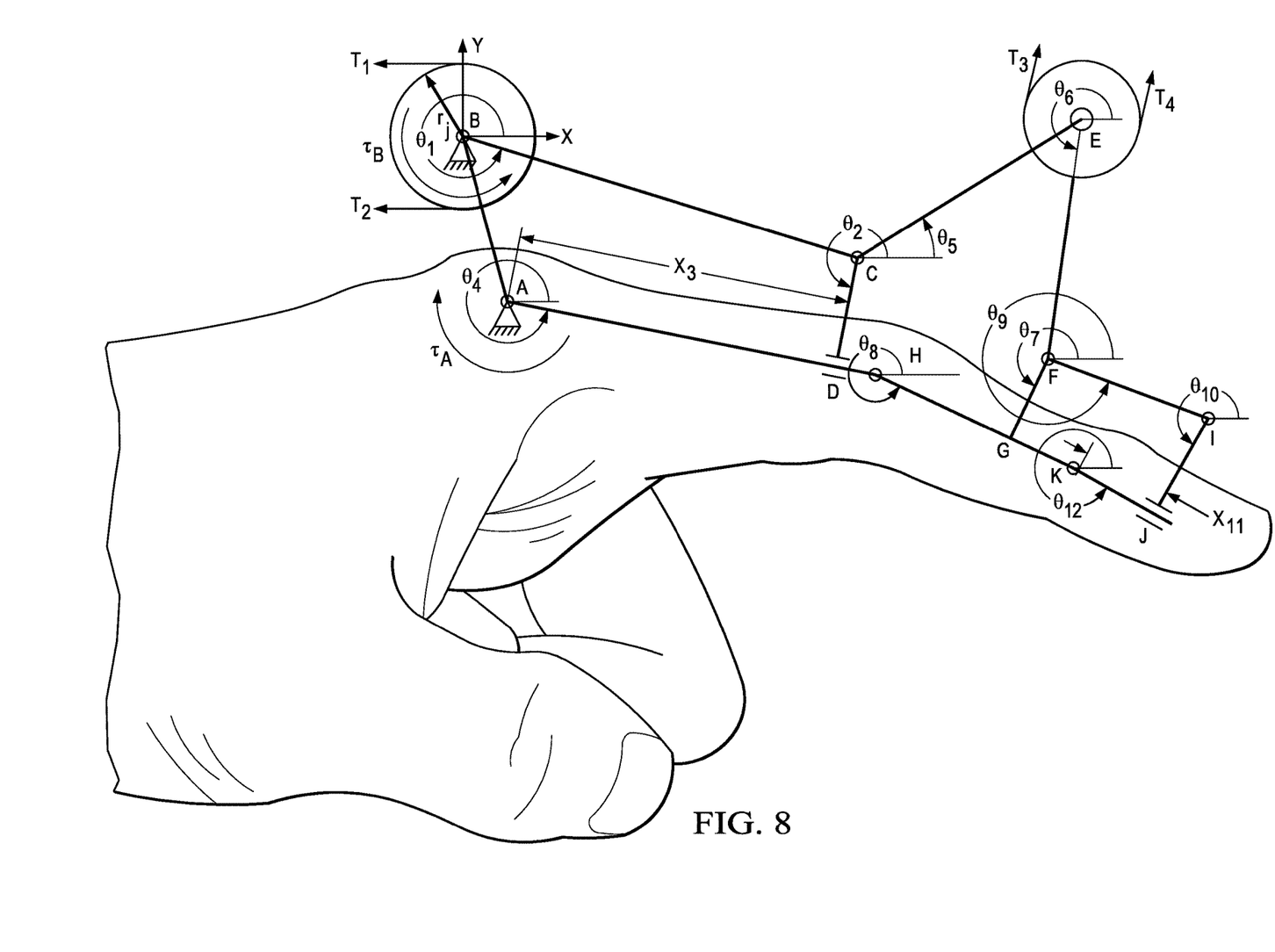
FIG. 8 illustrates a kinematic model of a robotic finger exoskeleton, in accordance with at least some embodiments of the present disclosure.

FIG. 8 illustrates a kinematic model of a robotic finger exoskeleton and identifies variables used in the following equations. Equation (1) may illustrate the kinematics of the MCP chain. Equation (2) may represent the differential of equation (1) solved for $\delta\theta_1$ $\delta x_3$. Equations (3) and (4) may represent the use of the principle of virtual work and, assuming friction at joints to be negligible, to relate the torque at the MCP joint to that at the exoskeleton joint. Equation (5) may represent the moment arm at the MCP joint. Equations (6) and (7) represent the kinematics of the PIP and DIP chains, respectively.

$$l_{BC}e^{i\theta_1} + l_{CD}e^{i\theta_2} + x_3 e^{i(\theta_4-\pi)} = x_A + iy_A \quad (1)$$

$$\begin{bmatrix} -l_{BC}\sin\theta_1 & \cos\theta_4 \\ l_{BC}\cos\theta_1 & \sin\theta_4 \end{bmatrix} \begin{bmatrix} \delta\theta_1 \\ \delta x_3 \end{bmatrix} = \begin{bmatrix} l_{CD}\sin\theta_2 + x_3\sin\theta_4 \\ -l_{CD}\cos\theta_2 - x_3\cos\theta_4 \end{bmatrix} \delta\theta_4 \quad (2)$$

$$\tau_B \delta\theta_1 = \tau_A \delta\theta_4 \quad (3)$$

$$T_2 - T_1 = \frac{\tau_B}{r_j} = \frac{\tau_A}{r_j\left(\frac{\delta\theta_1}{\delta\theta_4}\right)} \quad (4)$$

$$r_j\left(\frac{\delta\theta_1}{\delta\theta_4}\right) \quad (5)$$

$$l_{CE}e^{i\theta_5} + l_{EF}e^{i\theta_6} + l_{FG}e^{i\theta_7} + l_{GH}e^{i(\theta_8-\pi)} + l_{HD}e^{i(\theta_4-\pi)} + l_{DC}e^{i(\theta_2-\pi)} = 0 \quad (6)$$

$$l_{FI}e^{i\theta_9} + l_{IJ}e^{i\theta_{10}} + x_{11}e^{i(\theta_{12}-\pi)} + l_{KG}e^{i(\theta_8-\pi)} + l_{GF}e^{i(\theta_7-\pi)} = 0 \quad (7)$$

Figure 9:
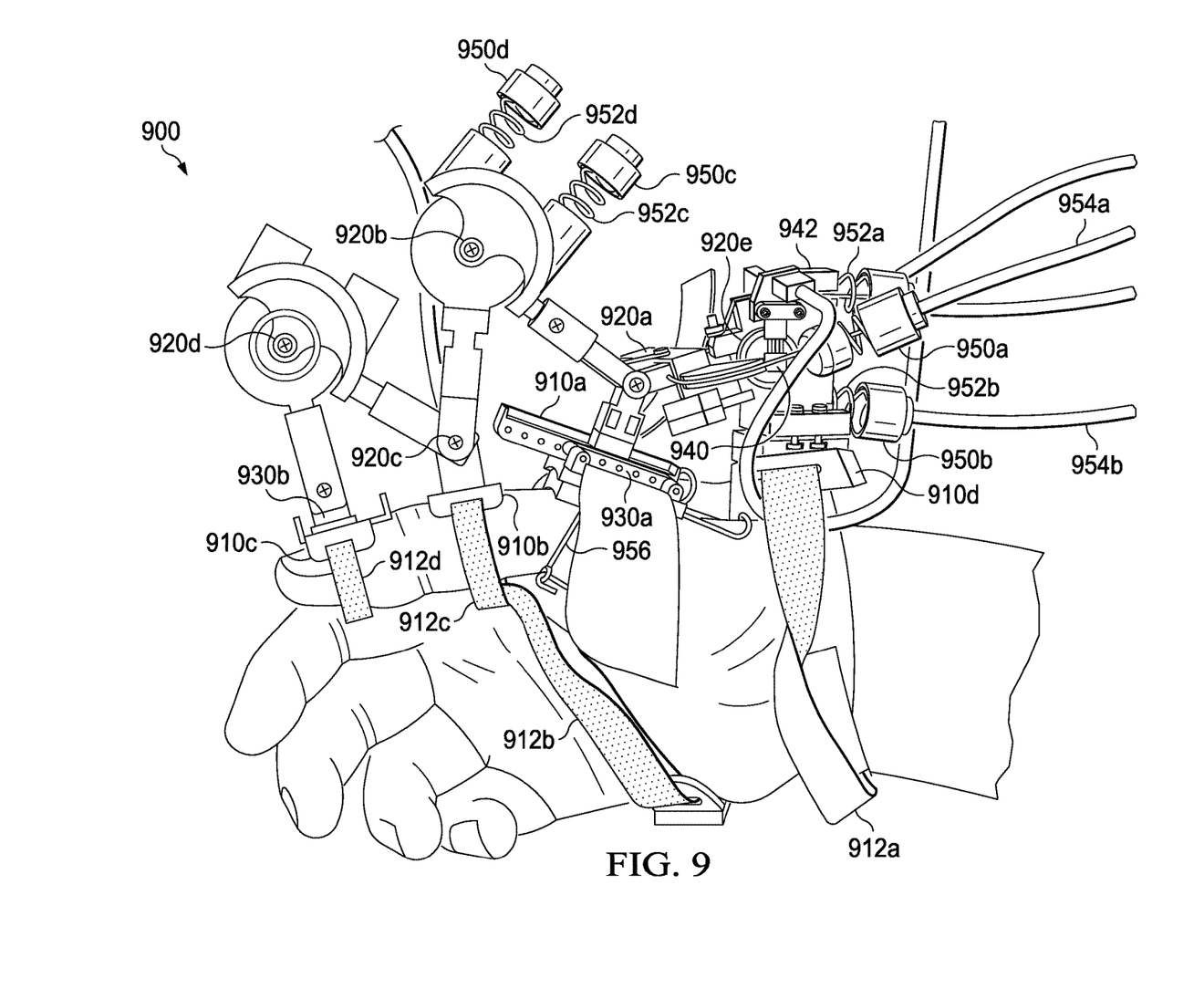
FIG. 9 illustrates an example embodiment of a robotic thumb exoskeleton, in accordance with at least some embodiments of the present disclosure.

FIG. 9 illustrates an example embodiment of a robotic thumb exoskeleton. Robotic thumb exoskeleton 900 may include a plurality of mounting components 910a, 910b, 910c, and 910d. These may be coupled with attachment straps 912a, 912b, 912c, and 912d. Thumb exoskeleton 900 may also include a plurality of joints, 920a, 920b, 920c, 920d, and 920e. Thumb exoskeleton 900 may additionally include sliding joints 930a and 930b. Thumb exoskeleton 900 may also include sensors 940, which may be coupled to data cables 942. Thumb exoskeleton 200 may further include series elastic actuators (SEAs) 950a, 950b, 950c, and 950d. These may include spring elements 952a, 952b, 952c, and 952d.

Mounting components 910 may be any component or device used to wrap thumb exoskeleton 900 about a thumb of a user of thumb exoskeleton 900. Mounting components 910 may be similar to mounting components 110 shown in FIG. 1. In some embodiments, mounting components 910 may be configured to support more than one finger exoskeleton 100 (shown in FIG. 1) and/or thumb exoskeleton 900. For example, mounting component 910a may support up to a combination of five distinct finger and thumb exoskeletons.

Mounting components 910 may be attached to a user of thumb exoskeleton 900 using attachment straps 912. Attachment straps 912 may be similar to attachment straps 112 shown in FIG. 1. While attachment straps 912a through 912d are illustrated in FIG. 9, it will be appreciated that any number of attachment straps 912 may be used to securely and comfortably attach thumb exoskeleton 900 to a user.

Joints 920 may be any juncture of thumb exoskeleton at which movement may occur. The movement may be rotation, lateral motion, or any other motion. Joints 920 may be similar to joints 120 shown in FIG. 1. The number and amount of movement of joints 920 may be selected such that thumb exoskeleton 900 provides comfortable and kinematically accurate movement. For example, thumb exoskeleton 900 may include a first joint 920a which is coupled to SEAs 950a and 950b. SEAs 950 and associated spring elements 952 may be described in more detail with respect to FIGS. 4 through 6.

In addition to joints 920, thumb exoskeleton 900 may also include sliding joints 930. Sliding joints 930 may include a slider and a track that are coupled such that the slider may slide along the track. This may provide a motion at the joint defined by the track. Sliding joints 930 may be similar to sliding joints 130 shown in FIG. 1. Sliding joints 130 may translate any force generated by the exoskeleton, which is not normal to the joint, into a sliding motion. This may prevent forces being generated against the joints themselves. For example, a force generated at joint 920e may not be directly normal to the thumb phalange. Thus, whatever portion of the force was not normal may be exerted against the MCP joint. By using sliding joints 930, rather than exerting the non-normal force against the MCP joint, the force instead causes sliding joints 930 to slide. In other words, employing sliding joints 930 as the interface between the thumb phalange and thumb exoskeleton 900 may ensure that only normal reaction forces are applied on the thumb phalanges in all configurations. Any lateral force may result in the translation of the slider until only the normal reaction force exists between the two. If sliding joints 930 is not used, the normal reaction force component may contribute to generating a moment at the joint while the lateral component may simply load the joint without resulting in any joint moment.

Joint 920e may replicate and provide motive force for part of the motion of the carpometacarpal (CMC) joint. For example, joint 920e may support flexion and extension of the CMC joint. Joint 920e may be coupled to mounting component 910d via framework of thumb exoskeleton 900. Joint 920e may also be connected to joint 920a via framework. Joints 920e and 920a may be orthogonal to each other at the base of the thumb of a user. Joint 920a may replicate and provide motive force for part of the motion of the MCP joint. For example, joint 920a may support flexion and extension of the MCP joint. Joint 920a may be coupled to sliding joint 930a via framework of thumb exoskeleton 900. Joint 920a may also be connected to joint 920b via framework. Joint 920b may provide passive motion to the MCP joint, for example, allowing lateral motion of a user's finger about the MCP joint. Joint 920b may be coupled to SEAs 950c and 950d which may provide motive force to joint 920b. This may provide motive force to thumb exoskeleton 900 when replicating the movement of the MCP joint. Joint 920b may be connected to joint 920c via framework. Joint 920c may be a hinge joint allowing passive rotation about joint 920c. Joint 920c may be connected to joint 920d through framework. Joints 920c and 920d may cooperatively replicate the motion of the interphalangeal (IP) joint. For example, the rotation about joints 920c and 920d may allow movement in the same plane passing approximately through the center of the user's thumb, or in other words, a sagittal plane of the thumb. In this way, when a user contracts their finger about the IP joint, the MCP joint is also contracted to a certain extent. Joint 920d may be connected to sliding joint 930b via framework of thumb exoskeleton 900.

In some embodiments, only some of the joints may utilize sliding joints 930. For example, as shown in FIG. 9, while the MCP and IP joints may utilize sliding joints 930 to protect against non-normal forces, the CMC joints may not utilize a sliding joint. This may allow for greater range of motion without requiring an additional motor. For example, by using joints 120c and 120d to replicate the motion of the IP joint, the IP joint has much greater range of motion without interference from the exoskeleton. However, if sliding joints 930 were used at mounting component 910d rather than a fixed point connection, an additional motor may be introduced to cover the additional degree of freedom. In some embodiments, each finger joint may be protected by sliding joints 930. This may lead to the coupling of additional motors to some of joints 920 of thumb exoskeleton 900.

Thumb exoskeleton 900 may also include sensor 940. Sensors 940 may be similar to sensors 140 shown in FIG. 1. Various features and embodiments of sensors 940 may be discussed in more detail with reference to FIG. 3. Information and/or data sensed by sensor 940 may be passed along data cables 942 to a computing device. In some embodiments, sensors 940 may wirelessly transmit sensed information and/or data, rather than transmitting the data along data cables 942. In some embodiments, information and/or data from sensor 940 may be collected at one or more points on thumb exoskeleton 900 and then passed from the one or more collection points to a computing device.

In some embodiments, the thumb phalanges are used as part of the linkage with thumb exoskeleton 900, including joints 920, sliding joints 930, and framework, to avoid any misalignment problems. For example, there may be four phalange-exoskeleton closed-loop kinematic chains to avoid joint axes misalignment problem. The CMC chain may consist of four links with three rotational joints (i.e., joints 920b, 920d, and 920e) and two translational joints (i.e., sliding joint 930a and 930b) resulting in two degrees of freedom. In other words, as a four-bar linkage may be created there may be only two degrees of freedom (e.g., flexion and extension) and only a single motive source may be used to replicate the motion of the joint. Orthogonal pulleys may actuate joints 920 (e.g., 920b and 920d). In some embodiments, the orthogonal pulleys may be actuated by independent SEAs. The pulleys may be similar to the pulleys described with respect to FIGS. 2-6.

Figure 10:
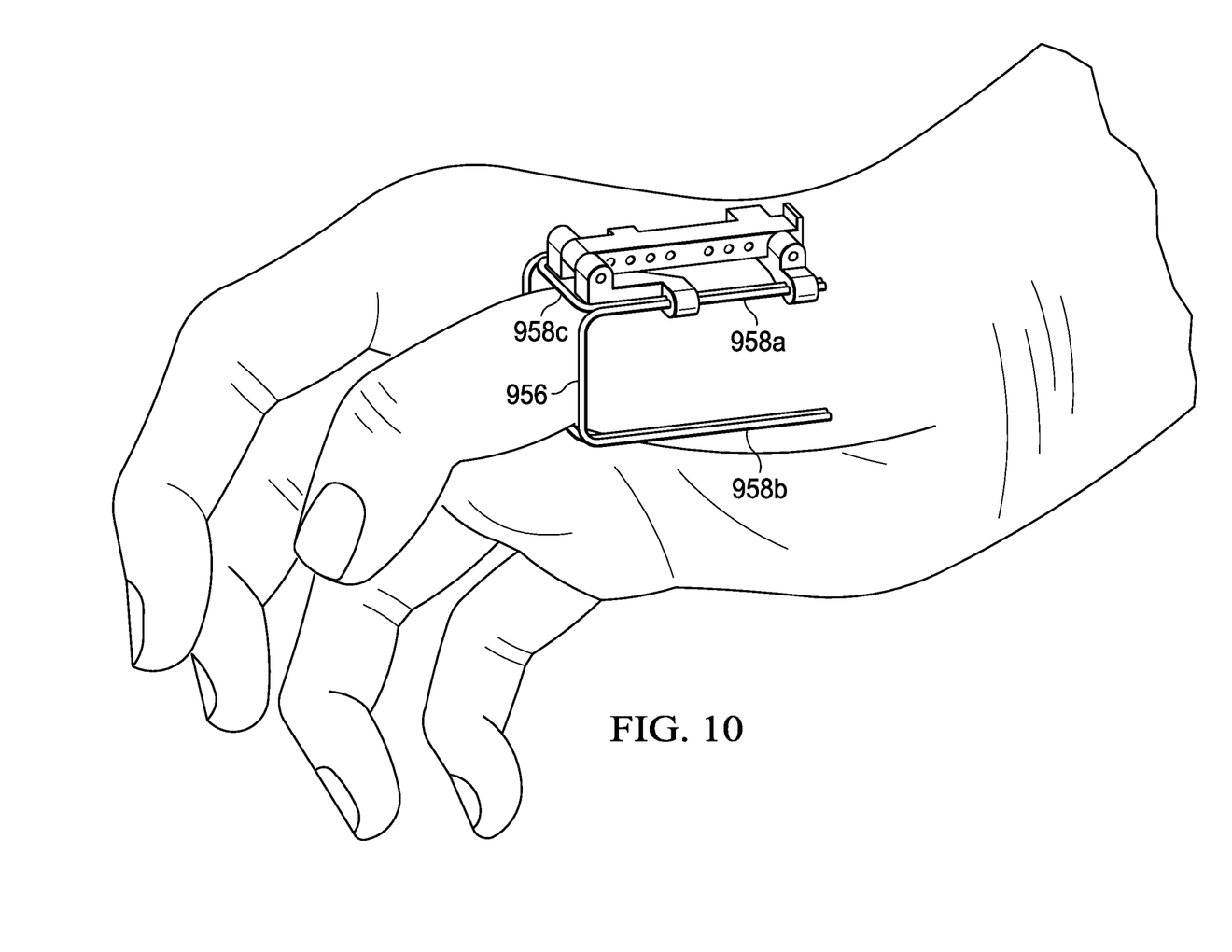
FIG. 10 illustrates an example embodiment of an attachment to connect a thumb exoskeleton to the thumb of a user, in accordance with at least some embodiments of the present disclosure.

The four-bar linkage mechanism requires that thumb exoskeleton 900 be rigidly attached to the metacarpal bone of the thumb. FIG. 10 illustrates an example embodiment of an attachment to connect a thumb exoskeleton to the thumb of a user. Attachment 956 may be used to attach thumb exoskeleton 900 to the metacarpal bone. Attachment 956 may be formed of galvanized steel wire or any other suitable attachment mechanism. Attachment 956 may form a ring around the MCP joint and may include four struts 958 that protrude downward and rest against the metacarpal bone. Struts 958 may be placed such that the thenar eminence muscles may protrude through the windows of the struts during contraction. Attachment 956 may provide structural stability for thumb exoskeleton 900 such that the loads generated by thumb exoskeleton 900 are transferred and distributed onto the metacarpal bone. In some embodiments, medical tape, velcro, or any other suitable material may be used to secure attachment 956 to the metacarpal bone and may prevent movement between thumb exoskeleton 900 and the thumb of the user.

In other embodiments, the CMC chain may consist of five links with two rotational joints (i.e., joints 920b and 920d) and one translational joint 930b resulting in two degrees of freedom (e.g., flexion and extension). A five-bar linkage may not require an attachment to the metacarpal bone. The use of two joints 920 may achieve the desired torques at the CMC and MCP flexion-extension joints.

Figure 11:
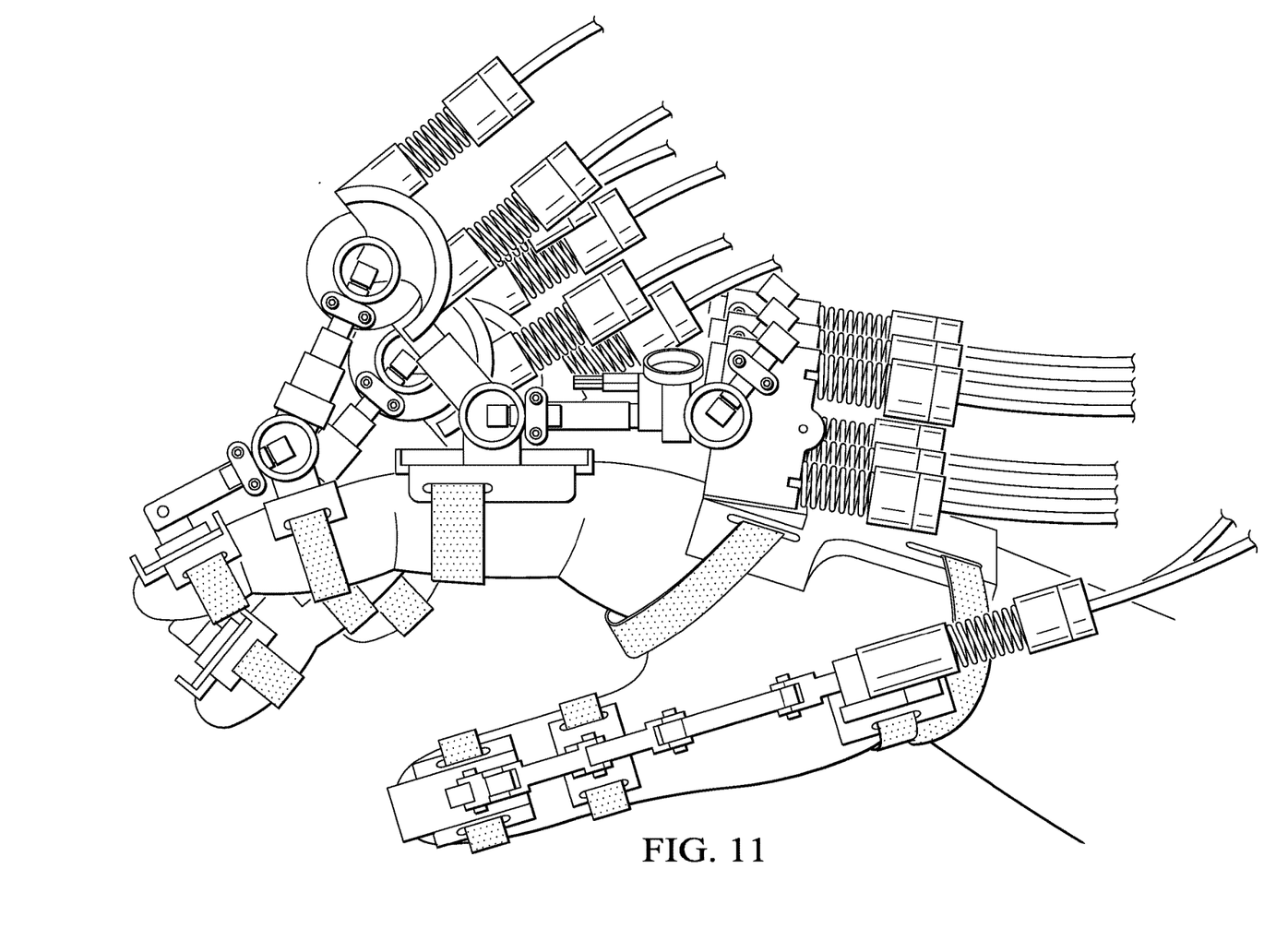
FIG. 11 illustrates an example of a robotic hand exoskeleton, in accordance with at least some embodiments of the present disclosure.

FIG. 11 illustrates an example of a robotic hand exoskeleton. For example, as shown in FIG. 11, a plurality of finger exoskeletons may be utilized, acting in concert, to provide a robotic exoskeleton for a hand rather than for an individual finger. As shown in FIG. 11, each of the digits from the index finger to the pinky finger may utilize a finger exoskeleton similar to finger exoskeleton 100. The thumb exoskeleton may operate on similar principles, but may provide three degrees of freedom for the CMC and metacarpophalangeal (MP) joints, and providing one degree of freedom for the IP joint.

The present disclosure may be used in a wide-variety of applications. While reference may be made to a finger, it will be appreciated that the principles extend to a hand as well. A finger exoskeleton in accordance with the present disclosure may be beneficial for stroke patients who may have lost various hand or finger functions. By using this device, an exercise regime may be implemented where a patient may be able to perform exercises with a certain amount of assistance from a finger exoskeleton. For example, a pre-programmed exercise routine may be used, or a physical therapist may give a specific exercise routine. In some embodiments, a therapist may be the user of finger exoskeleton in a learning mode when helping finger exoskeleton to "learn" the exercise motions to be followed. For example, a therapist may go through a series of motions and sensors may measure locations, forces, and/or motor speeds that may be implemented to recreate that motion. Then a patient may use the finger exoskeleton to go through the learned motions. In this way, a physical therapist may not need to be present as a patient exercises using the finger exoskeleton.

In addition to the context of medical recoveries, the same principles may be applied to general fitness equipment. For example, a user of finger exoskeleton may go through a series of exercises in which finger exoskeleton provides resistance, rather than assistance, to the user as they go through a series of motions. In this way, a user of finger exoskeleton may be given a specific exercise routine. Similarly, just as a physical therapist could go through a learning mode to teach finger exoskeleton a particular set of motions, a personal trainer could also provide a personalized set of exercises for a user of finger exoskeleton.

The present disclosure may also have application in the entertainment industry. For example, video game systems may provide responsive motions to physically re-create motions or movement happening in the video game. Alternatively, environmental effects may be recreated. For example, if a user were to place their hand under water in a video game, the forces operating on a finger of that hand may be recreated using a finger exoskeleton. In this way, a more interactive and engrossing video game experience may be developed.

Additionally, the present disclosure may have application for the military. For example, a finger exoskeleton may provide increased strength or endurance to a soldier using a finger exoskeleton, beyond their own physical limitations. For example, as a sensor senses a soldier moving their finger in a certain way, finger exoskeleton may exert additional force in that same direction to lessen the effort required by the soldier. Additionally, the speed of a soldier's motions may be accelerated. For example, if a motion is sensed by the sensors of a finger exoskeleton, for example, a squeezing motion, that motion may be completed at an accelerated rate by the finger exoskeleton. The finger exoskeleton may also allow soldiers to manipulate heavy loads. For example, as a soldier manipulates a certain load with their hands, the soldier's effort may be augmented by the finger exoskeleton also exerting additional force in the same direction the soldier may be working. The present disclosure may also be beneficial in any other setting in which heavy loads may need to be manipulated, for example and in no way limiting, emergency response to accidents, industrial processing, or manufacturing.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. For example, various embodiments may perform all, some, or none of the steps described above. Various embodiments may also perform the functions described in various orders.

Although the present disclosure has been described above in connection with several embodiments; changes, substitutions, variations, alterations, transformations, and modifications may be suggested to one skilled in the art, and it is intended that the present disclosure encompass such changes, substitutions, variations, alterations, transformations, and modifications as fall within the spirit and scope of the appended claims.

What is claimed is:

1. A finger exoskeleton comprising:
   a plurality of joints;
   a plurality of sensors configured to measure rotation of at least some of the plurality of joints of the finger exoskeleton;
   a first series elastic actuator comprising a spring element, the first series elastic actuator configured to rotate at least one of the plurality of joints;
   a sliding joint configured to translate one or more lateral forces applied to the at least one of the plurality of joints into a normal reaction force, the one or more lateral forces causing the sliding joint to slide; and
   a computing device configured to control operation of the first series elastic actuator based on a torque of the at least one of the plurality of joints, the torque determined at least based on the spring element and rotation of the at least one of the plurality of joints.

2. The finger exoskeleton of claim 1, wherein the first series elastic actuator further comprises Bowden cables.

3. The finger exoskeleton of claim 2, wherein a sheath of the Bowden cable is fixed to the spring element.

4. The finger exoskeleton of claim 2, wherein an inner cable of the Bowden cable is fixed to the spring element.

5. The finger exoskeleton of claim 1, wherein at least one of the plurality of joints are manufactured with additive manufacturing techniques.

6. The finger exoskeleton of claim 1, further comprising a second series elastic actuator independently operable from the first series elastic actuator.

7. The finger exoskeleton of claim 1, wherein at least one of the plurality of joints allows for passive motion.

8. The finger exoskeleton of claim 1, wherein the torque is determined by the equation:

$$\tau_{joint} = K_{spring}(\theta_{joint} - \theta_{actuator})$$

9. The finger exoskeleton of claim 1, the first series elastic actuator further comprising a motor.

10. The finger exoskeleton of claim 1, wherein the finger exoskeleton operates in a force-control mode of operation.

11. The finger exoskeleton of claim 1, further comprising an attachment connecting the finger exoskeleton to a metacarpal bone of a thumb of a user and configured to maintain contact with the thumb while the thumb is in motion.

12. The finger exoskeleton of claim 1, wherein at least one of the plurality of joints is configured to be rotated by a plurality of series elastic actuators.

13. A method comprising:
measuring a first rotation of a joint of a robotic finger exoskeleton;
detecting a second rotation of a motor coupled to a series elastic actuator;
translating one or more lateral forces applied to the joint of the robotic finger into a normal reaction force;
determining a torque of the joint of the robotic finger exoskeleton based at least on the first rotation and a spring element of the series elastic actuator; and
modifying an operation of the series elastic actuator based on the torque.

14. The method of claim 13, further comprising providing an assistive force to a user of the robotic finger exoskeleton.

15. The method of claim 13, wherein modifying the operation of the series elastic actuator comprises ceasing a rotation of the joint of the robotic finger exoskeleton contrary to a previous planned motion.

16. A hand exoskeleton comprising:
a plurality of finger exoskeletons, each finger exoskeleton comprising:
a plurality of joints;
a plurality of sensors configured to measure rotation of at least some of the plurality of joints of the finger exoskeleton; and
a series elastic actuator comprising a spring element, the series elastic actuator configured to rotate at least one of the plurality of joints;
a sliding joint configured to translate one or more lateral forces applied to the at least one of the plurality of joints into a normal reaction force, the one or more lateral forces causing the sliding joint to slide; and
a computing device configured to control operation of the series elastic actuator based on a torque of the at least one of the plurality of joints, the torque determined at least based on the spring element and a rotation of the at least one of the plurality of joints.

17. The hand exoskeleton of claim 16, wherein the series elastic actuator further comprises Bowden cables.

18. The hand exoskeleton of claim 16, wherein a sheath of the Bowden cables is fixed to the spring element.

19. The hand exoskeleton of claim 16, wherein an inner cable of the Bowden cable is fixed to the spring element.

\* \* \* \* \*